(12) United States Patent
Wang et al.

(10) Patent No.: US 8,548,282 B2
(45) Date of Patent: Oct. 1, 2013

(54) FIBER IN-LINE MACH-ZEHNDER INTERFEROMETER (MZI) DEVICE

(75) Inventors: Dongning Wang, Kowloon (HK); Minwei Yang, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 189 days.

(21) Appl. No.: 13/170,647

(22) Filed: Jun. 28, 2011

(65) Prior Publication Data

US 2012/0188553 A1   Jul. 26, 2012

Related U.S. Application Data

(60) Provisional application No. 61/434,829, filed on Jan. 21, 2011.

(51) Int. Cl.
*G02B 6/00* (2006.01)
(52) U.S. Cl.
USPC .............. 385/12; 385/13; 385/15; 385/31; 385/123; 385/129
(58) Field of Classification Search
USPC ................ 385/12, 13, 15, 31, 123, 129
See application file for complete search history.

(56) References Cited

U.S. PATENT DOCUMENTS 6,856,737 B1 * 2/2005 Parker et al. ............... 385/122
6,901,194 B2 * 5/2005 Charlton et al. ........... 385/122

OTHER PUBLICATIONS

Du et al., "Thermally tunable dual-core photonic bandgap fiber based on the infusion of a temperature-responsive liquid", Optics Express, Mar. 17, 2008, vol. 16, No. 6, 7 pgs.
Kou et al, "Wave guiding properties and sensitivity of D-shaped optical fiber microwire devices", Applied Physics B, Laser and Optics, Aug. 2010, 5 pgs.
Kuhlmey et al., "Fluid-Filled Solid-Core Photonic Bandgap Fibers", Journal of Lightwave Technology, Jun. 1, 2009, vol. 27, No. 11, pp. 1617-1630.
Mangan et al., "Experimental study of dual-core photonic crystal fibre", Electronics Letters, Aug. 3, 2000, vol. 36, No. 16, pp. 1358-1359.
Padden et al., "coupling in a twin-core microstructured polymer optical fiber", Applied Physics Letters, Mar. 8, 2004, vol. 84, No. 10, 1689-1691.

(Continued)

*Primary Examiner* — Jennifer Doan
(74) *Attorney, Agent, or Firm* — KPPB LLP (57) ABSTRACT

A fiber-inline MZI device for temperature sensing or refractive index (RI) sensing, the device comprising: a section of a Photonic Crystal Fiber (PCF) having at least two air holes infiltrated with a liquid analyte to form a waveguide channel, the liquid analyte forming rods in the PCF; wherein the rods leave an interference fringe pattern in the transmission spectrum when light is injected into the PCF, and fringe dips are tracked over a wide wavelength range in order to sense the temperature or refractive index.

13 Claims, 12 Drawing Sheets

(56) References Cited

OTHER PUBLICATIONS

Town et al., "Microstructured optical fiber refractive index sensor", Optics Letters, Mar. 15, 2010, vol. 35, No. 6, pp. 856-858.

Toyoda et al., "The temperature dependence of the refractive indices of fused silica and crystal quartz", J. Phys. D: Appl. Phys, 1983, vol. 16, pp. L97-L100.

Wang et al., "coupling in dual-core photonic bandgap fibers: theory and experiment", Optics Express, Apr. 16, 2007, vol. 15, No. 8, pp. 4795-4804.

Wang et al., "Femtosecond laser-assisted selective infiltration of microstructured optical fibers", Optics Express, Aug. 16, 2010, vol. 18, No. 17, pp. 18056-18060.

Wang et al., "High-Temperature Sensing Using Miniaturized Fiber In-Line Mach-Zehnder Interferometer", IEEE Photonics Technology Letters, Jan. 1, 2010, vol. 22, No. 1, pp. 39-41.

Wu et al., "Ultrasensitive photonic crystal fiber refractive index sensor", Optics Letters, Feb. 1, 2009, vol. 34, No. 3, pp. 322-324.

Yuan et al., "Refractive Index Sensing in an All-Solid Twin-Core Photonic Bandgap Fiber", IEEE Sensors Journal, Jul. 2010, vol. 10, No. 7, pp. 1192-1199.

* cited by examiner

FIBER IN-LINE MACH-ZEHNDER INTERFEROMETER (MZI) DEVICE

CROSS-REFERENCE TO RELATED APPLICATION

The present invention claims priority under 35 U.S.C. §119(e) to U.S. Provisional Patent Application No. 61/434,829 filed Jan. 21, 2011, the disclosure of which is incorporated by reference herein in its entirety.

TECHNICAL FIELD

The invention concerns a fiber-inline MZI device for temperature sensing or refractive index (RI) sensing.

BACKGROUND OF THE INVENTION

A Mach-Zehnder interferometer (MZI) is a device for determining the relative phase difference between two collimated beams from a coherent light source. The interferometer is used to measure small phase difference in one of the two beams caused by a small sample or the change in length of one of the paths.

A MZI usually contains two cascaded fiber components that function as a beam splitter and combiner. The temperature sensitivity of this device is typically small because the thermo coefficient of silica fiber is small.

Another type of MZI based on dual core photonic crystal fiber (PCF) has been developed. This kind of MZI requires a special design of the fiber for selective infiltration and therefore has difficulties for a broad application.

SUMMARY OF THE INVENTION

In a first preferred aspect of the invention, there is provided a fiber-inline MZI device for temperature sensing or refractive index (RI) sensing, the device includes:
  a section of a Photonic Crystal Fiber (PCF) having at least two air holes infiltrated with a liquid analyte to form waveguide channels, the liquid analyte forming rods in the PCF; and
  where the rods leave an interference fringe pattern in the transmission spectrum when light is injected into the PCF, and fringe dips are tracked over a wide wavelength range in order to sense the temperature or refractive index.

In another such embodiment, only two air holes may be infiltrated with the liquid analyte.

In still another such embodiment, at least one of the air holes that are infiltrated with the liquid analyte may be located directly adjacent to a core of the PCF.

In yet another such embodiment, the liquid analyte may have a higher refractive index value than background silica of the PCF such that the rods formed in the PCF are high RI rods.

In still yet another such embodiment, after the liquid analyte is infiltrated in the air holes, the liquid analyte may be solidified in the air holes by exposing UV light onto the PCF.

In still yet another such embodiment, if the wavelength shifts towards a shorter wavelength, the temperature may be sensed as increasing.

In still yet another such embodiment, the PCF may be a NKT Photonics LMA-10, with a hole diameter of 3.04 μm, a hole pitch of 6.26 μm and a length of about 10 cm.

In still yet another such embodiment, the background silica may have a refractive index of 1.444 and the liquid analyte has a refractive index of 1.47 with a thermo coefficient of −0.000392/° C.

In still yet another such embodiment, the liquid analyte may substantially fully infiltrate the two air holes of the section of the PCF.

In still yet another such embodiment, the PCF may have a single core or multi-core structure.

In a second aspect of the invention, there is provided a method for manufacturing a fiber-inline MZI device for temperature sensing or refractive index (RI) sensing, including:
  infiltrating at least two air holes of a Photonic Crystal Fiber (PCF) with a liquid analyte to form waveguide channels, the liquid analyte forming rods in the PCF;
  incrementally cutting back the PCF until a remaining section of the PCF has the at least two air holes completely filled with the liquid analyte to obtain an infiltrated PCF sample; and
  wherein the rods leave an interference fringe pattern in the transmission spectrum when light is injected into the PCF, and fringe dips are tracked over a wide wavelength range in order to sense the temperature or refractive index.

In one such embodiment, the method may further include fusing the infiltrated PCF sample with a single mode fiber on both ends of the infiltrated PCF sample.

In still another such embodiment, the method may further include heating the infiltrated PCF sample and recording transmission spectra.

In yet another such embodiment, the method may further include solidifying the liquid analyte after the liquid analyte is infiltrated in the air holes by exposing UV light.

BRIEF DESCRIPTION OF THE DRAWINGS

An example of the invention will now be described with reference to the accompanying drawings, in which.

DETAILED DESCRIPTION OF THE DRAWINGS

Photonic crystal fiber (PCF) is a type of microstructured optical fiber that contains a solid fiber core, surrounded by periodical arrays of air holes in the fiber cladding. Compared with a normal single mode fiber, a PCF has many interesting modal and dispersion properties. The air holes around the solid core make a PCF a platform for refractive index (RI) sensing. Liquid analyte with a higher RI value than that of the background silica is infiltrated into certain air hole(s) of a PCF. As the liquid which is infiltrated in the air holes has a higher RI value than that of the background silica, the two mode interference is generated by the PCF core mode and the guide mode supported by the two high RI rods. Consequently, light energy can be coupled from the fiber core mode to the rod mode due to the photonic bandgap (PBG) effect and thus producing wavelength window(s) of high and low transmission. The wavelength window(s) can be used for RI sensing and temperature measurement with high sensitivity and small detection limits. Using femtosecond laser assisted micro-machining, a selective infiltration of any air hole in the cross section of the PCF is performed. The high RI analyte rod in the PCF essentially forms a waveguide channel. The characteristics of the sensor constructed depend on the phase matching condition between the PCF core mode and the waveguide mode of the high RI rod.

Another type of RI sensor based on selective infiltration of air holes is achieved by use of a multi-core structure PCF. In the case of a dual core or multi core structure PCF, energy coupling between the two or more cores always exists, and hence the light energy can be transferred between these two cores. The coupling characteristics are strongly dependent on the distance between the two cores, the effective NA, the coupling length and the normalized frequency $\Lambda/\lambda$ (where $\Lambda$ is the pitch of the air holes and $\lambda$ is the free space wavelength), which results in an interference fringe pattern in the transmission spectrum. When the air holes between the two cores are filled with different RI analytes, the interference fringe pattern shifts and thus enabling RI sensing.

The selective infiltration of the two adjacent air holes at the innermost layer of the PCF can support a virtual core mode, which can interfere with the PCF fundamental mode and thus leaving an interference fringe pattern in the transmission spectrum. This is a new kind of mode coupling. The virtual core mode is generated from the higher order mode coupling between the two high RI analyte rods and has an effective RI lower than the background silica.

By selective infiltration of the two adjacent air holes of the innermost layer of commercially available PCF, a fiber in-line MZI device is fabricated with good robustness and can be applied for temperature sensing with extremely high sensitivity. The sensitivity is better than other sensors that depend on the thermo-optic effect of silica only. This is because the high RI analyte infiltrated usually has a much larger thermo coefficient than that of silica.

The MZI device can be used as a temperature and/or refractive index (RI) sensor with high sensitivity, and it has potential applications for on-off type optical switch. Also, a flexible sensor system operation can be achieved by tracking arbitrary/different fringe dips (peak) over a wide wavelength range.

Figure 1:
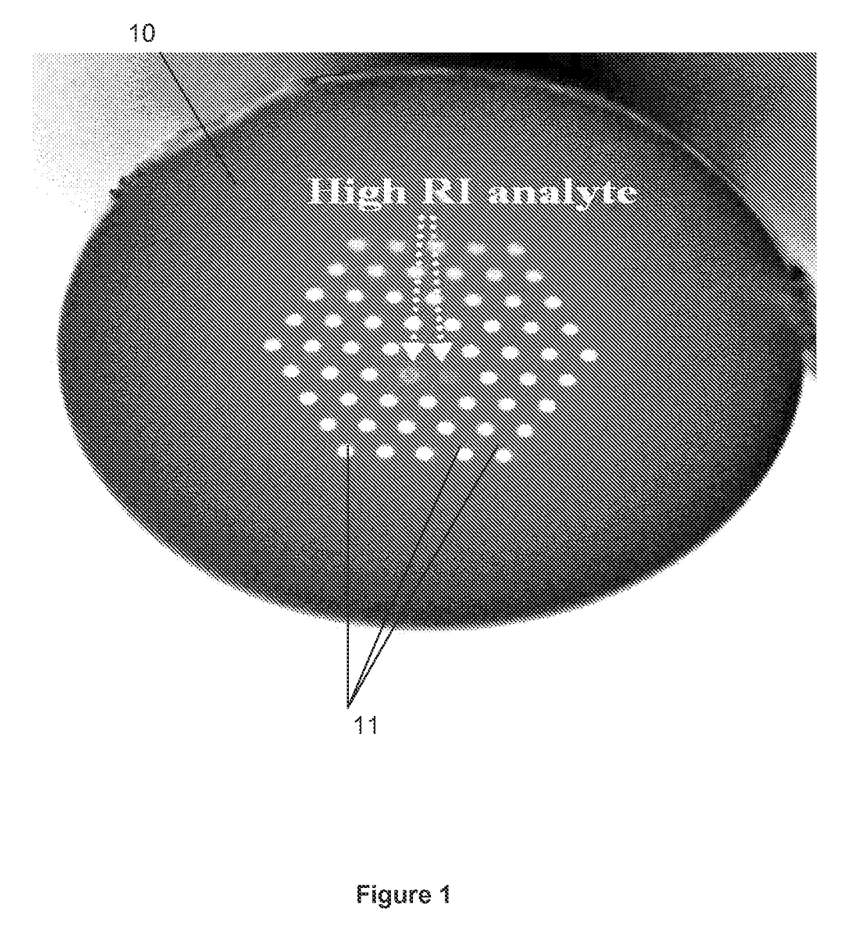
FIG. 1 is a cross sectional diagram of a Photonic Crystal Fiber (PCF) with two holes infiltrated with liquid analyte having refractive index (RI) values higher than that of the background silica of the PCF.
Figure 7:
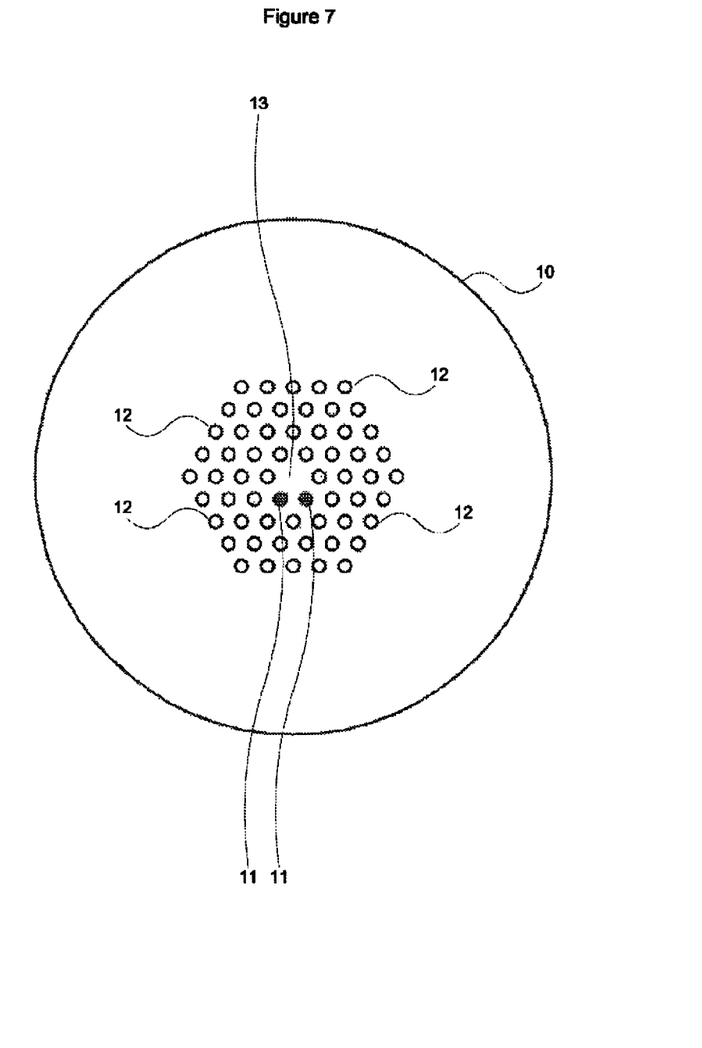
FIG. 7 is a schematic diagram of the PCF illustrated in FIG. 1.

Referring to FIGS. 1 and 7, an exemplary embodiment of a fiber-inline MZI device 9 is provided. The device 9 is formed in a section of a Photonic Crystal Fiber (PCF) 10 with multiple air holes 12. Two adjacent air holes 11 of the innermost layer of the PCF 10 are selectively infiltrated with liquid analyte. The innermost layer refers to holes 11 circumferentially adjacent to the solid core 13 of the PCF 10. It may be possible to infiltrate other holes adjacent to the solid core 13 of the PCF 10 apart from the ones illustrated. The PCF 10 is a NKT Photonics LMA-10, with a hole diameter of 3.04 µm and a hole pitch of 6.26 µm. The length of the PCF is ~10 cm.

The liquid analyte is infiltrated into the two air holes 11 of the PCF 10 due to the capillary effect. The liquid analyte has refractive index (RI) values higher than that of the background silica (RI=1.444) of the PCF 10 by femtosecond assisted micro-machining. For example, the liquid analyte may have an RI of 1.47 made by Cargille Labs and at 25° C., the wavelength is 589.3 nm with a thermo coefficient of −0.000392/° C. However, when a liquid analyte with a higher RI than this is infiltrated, the number of generated rod modes which can interfere with the core mode will increase, which makes the interference fringe also difficult to observe. The infiltration time is approximately 24 hours and the non-immersed PCF end is left open to allow a sufficiently long infiltrated length to be used. The infiltrated length of the PCF 10 is approximately 8.2 cm to 10 cm.

After the infiltration is completed, a cross section of the sample of the PCF 10 is observed with a microscope, as shown in FIG. 1. The PCF 10 is cut back starting from the non-immersed fiber end with visual assistance of a microscope. The PCF 10 is incrementally cut back until the remaining portion of the PCF 10 only contains a section of the PCF 10 where the two adjacent air holes 11 are completely filled with the RI liquid analyte. This ensures that the remaining PCF 10 is totally infiltrated with the liquid analyte in the desired holes 11. The cut back process is performed to further improve the spectral property by ensuring the holes 11 of the remaining PCF portion are infiltrated with the liquid analyte as fully as possible. By cutting back the PCF 10 in this way, it addresses problems due to the interference fringe in transmission spectra not being uniform either in visibility or in wavelength. When the transmission spectra is not uniform the reasons may be because: the two holes 11 may have different lengths of analyte due to the difference in infiltrating speed; or the two holes are not fully infiltrated with the liquid analyte and thus the excited waveguide rod modes have large loss in the remaining PCF 10; or the liquid analyte may have moved in the air hole 11.

Figure 10:
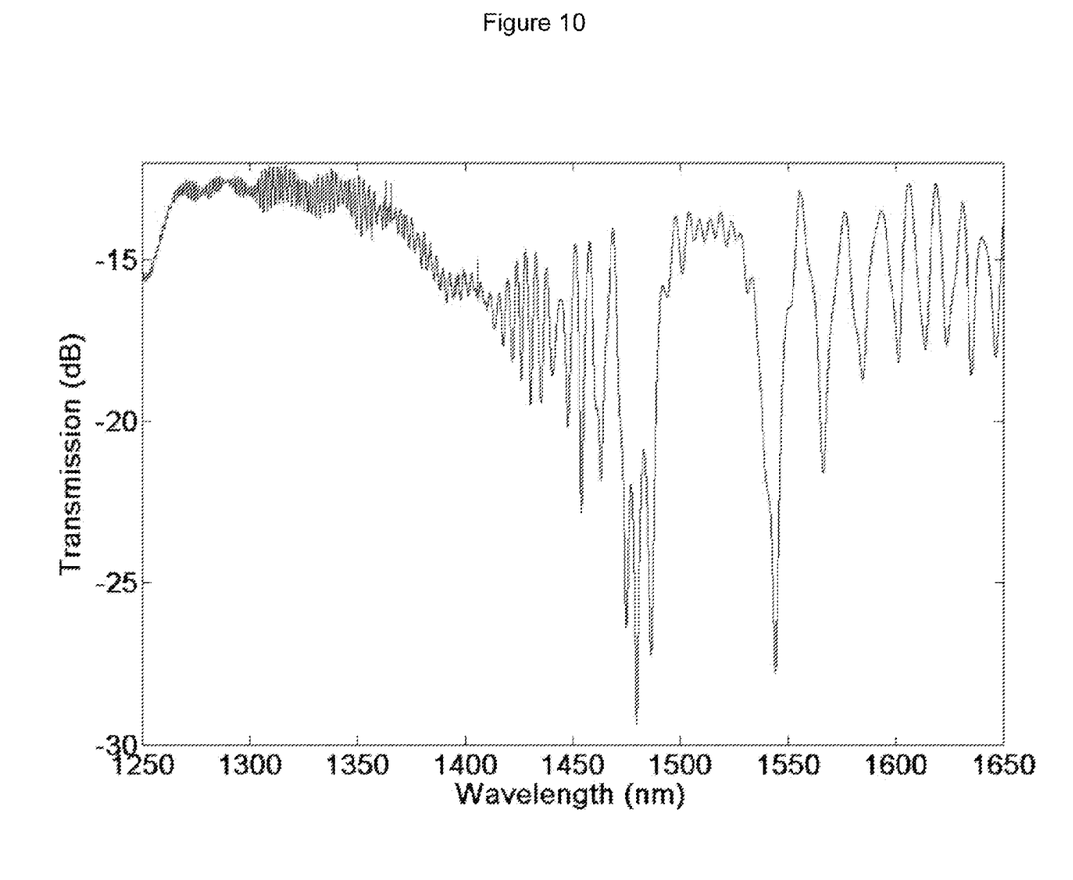
FIG. 10 is a chart depicting transmission spectrum of the sample at 20° C.

The infiltrated PCF sample is obtained after the cut back process. The infiltrated PCF sample is fused with single mode fiber on both ends and its transmission spectrum is measured. The infiltrated PCF sample is placed into an oven to measure its temperature response. The initial transmission spectrum (temperature is 20° C.) is shown in FIG. 10, which is recorded by an optical spectrum analyzer (AQ3619, Yokogawa), with the resolution of 0.1 nm.

Figure 11:
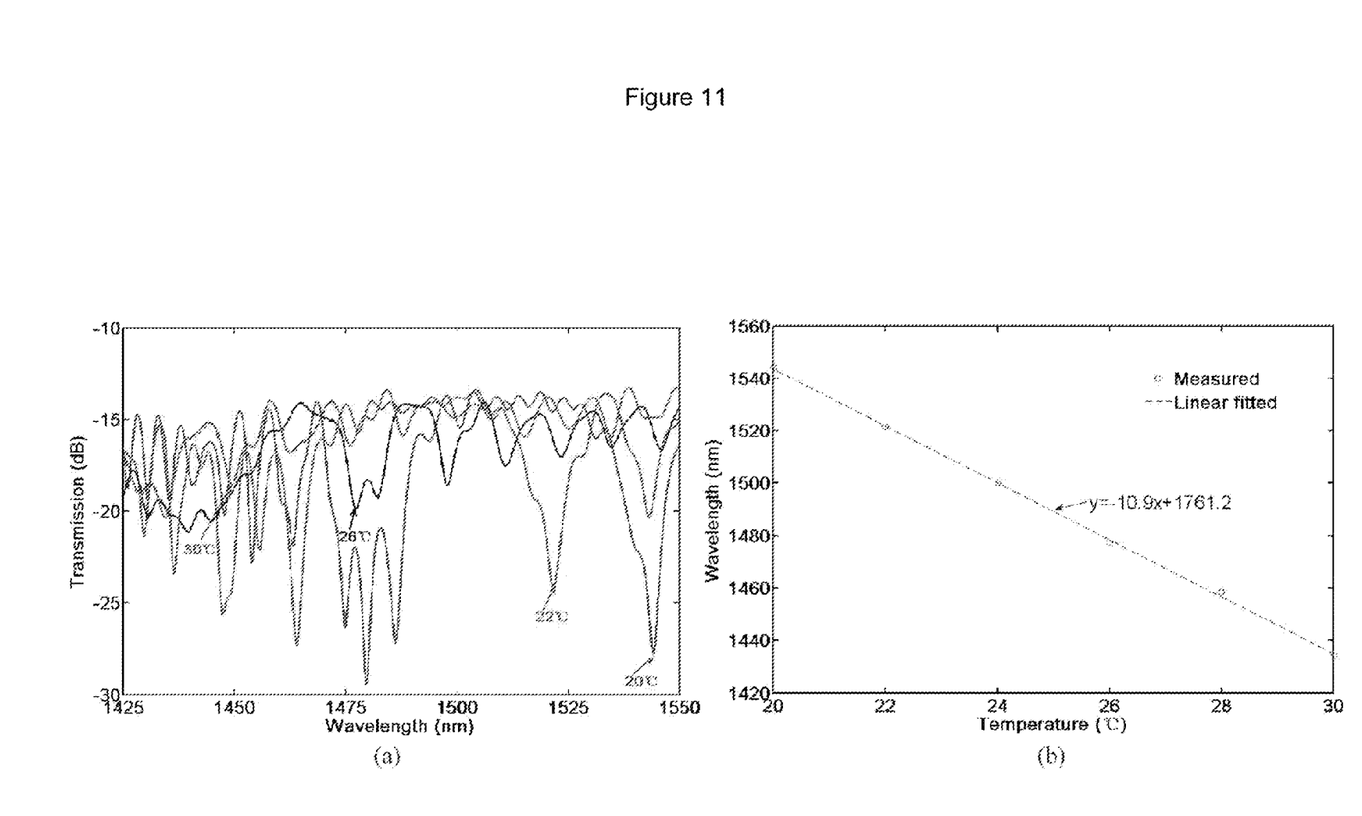
FIG. 11 is a set of charts depicting (a) selected plotting of transmission spectra evolution with temperature; and (b) temperature sensitivity of one fringe dip.

The infiltrated PCF sample is subsequently heated and the transmission spectra are recorded for the temperature range between 20° C. and 30° C., with a step of 2° C. When the temperature increases, the interference fringe pattern shifts toward the shorter wavelength, as shown in FIG. 11(a). The wavelength shift of one of the fringe dips (1544.1 nm at 20° C.) is monitored and its temperature response is shown in FIG. 11(b), where a temperature sensitivity of −10.9 nm/° C. can be obtained, corresponding to a RI sensitivity of 2.7×104 nm/RIU.

In FIG. 7, the two solid circles 11 proximal to the center 13 of the PCF 10 indicate the high refractive index (RI) analyte rods. After being fused with the single mode fiber, the holes 11 with the infiltrated liquid cannot be clearly observed by micro objective, since the air holes 12 in the outer layers of the PCF 10 will make the light focus difficult.

The principle of the device 9 is based on the interference between the PCF core mode and the hybrid mode generated from the coupling of the two $LP_{11}$ high order rod modes. If more holes 12 are infiltrated, the rod modes generated will result in a complicated coupling and thus the interference fringe would be complicated and the fringe peak would be difficult to trace. However, an interference fringe pattern is still generated.

The two selected air holes 11 essentially form a twin core photonic bandgap (PBG) structure which confines the light energy within the region between the two holes. When light is injected in the PCF 10, three kinds of fiber modes can be excited. The three fiber modes are: fiber core mode, LP01 like rod mode and the higher order $LP_{11}$ like rod mode. The infiltrated holes 11 are selected so as to excite stronger waveguide rod modes (compared with the holes 12 in the outer layer of the PCF 10) and makes the interference easily occur when both the core mode and the waveguide modes reaches the fusion splicing point of the PCF 10 and single mode fiber.

Figure 8:
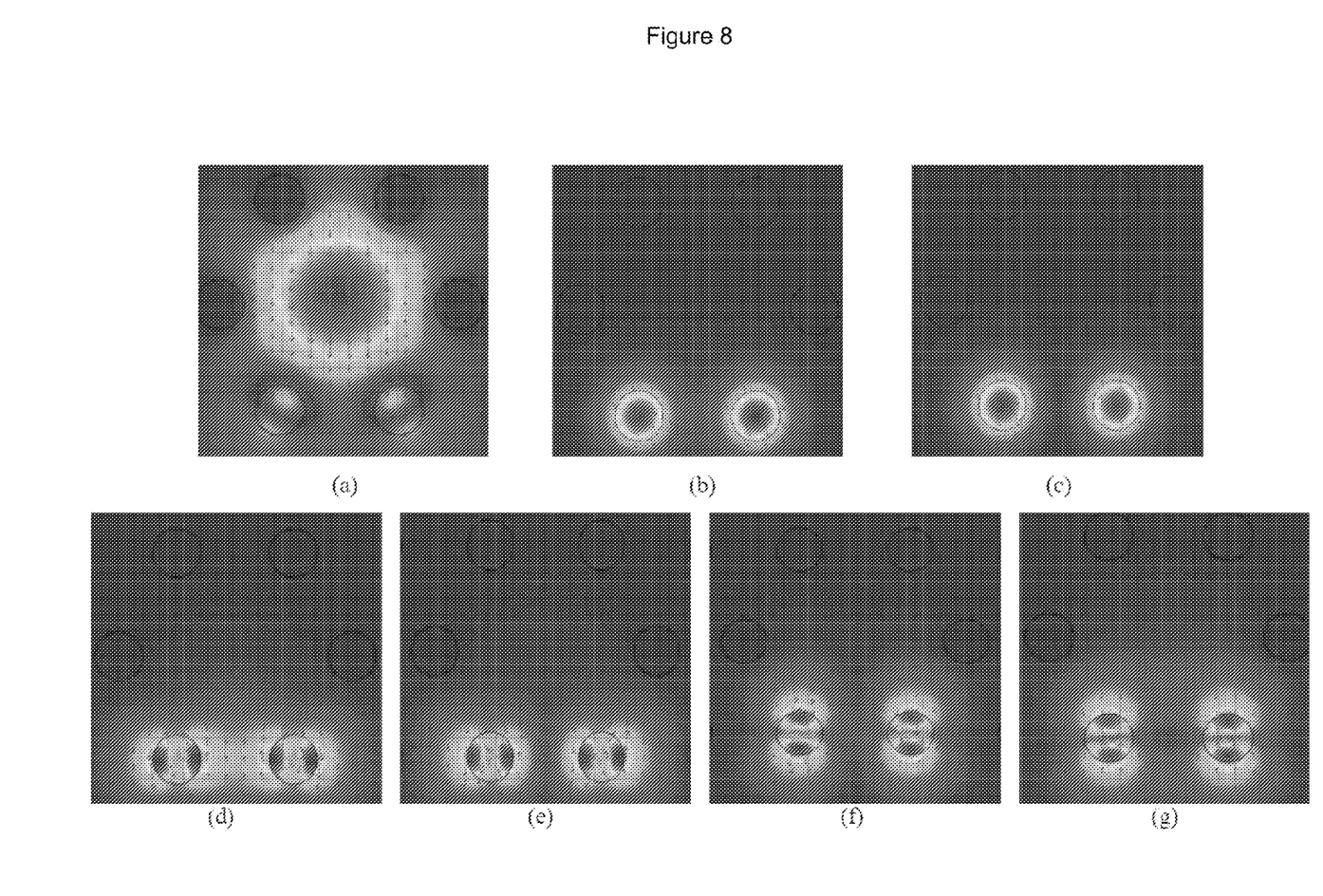
FIG. 8 is a set of images plotting the y polarization of seven modes.

Referring to FIGS. 8(a) to 8(g), through finite element method (FEM), the mode fields intensity profile of these modes can be calculated. All the seven modes are two folder degenerated however, for the sake of simplicity, only one polarization state (y polarization) is plotted. Mode A shown in FIG. 8(a) is the fiber core mode.

Figure 9:
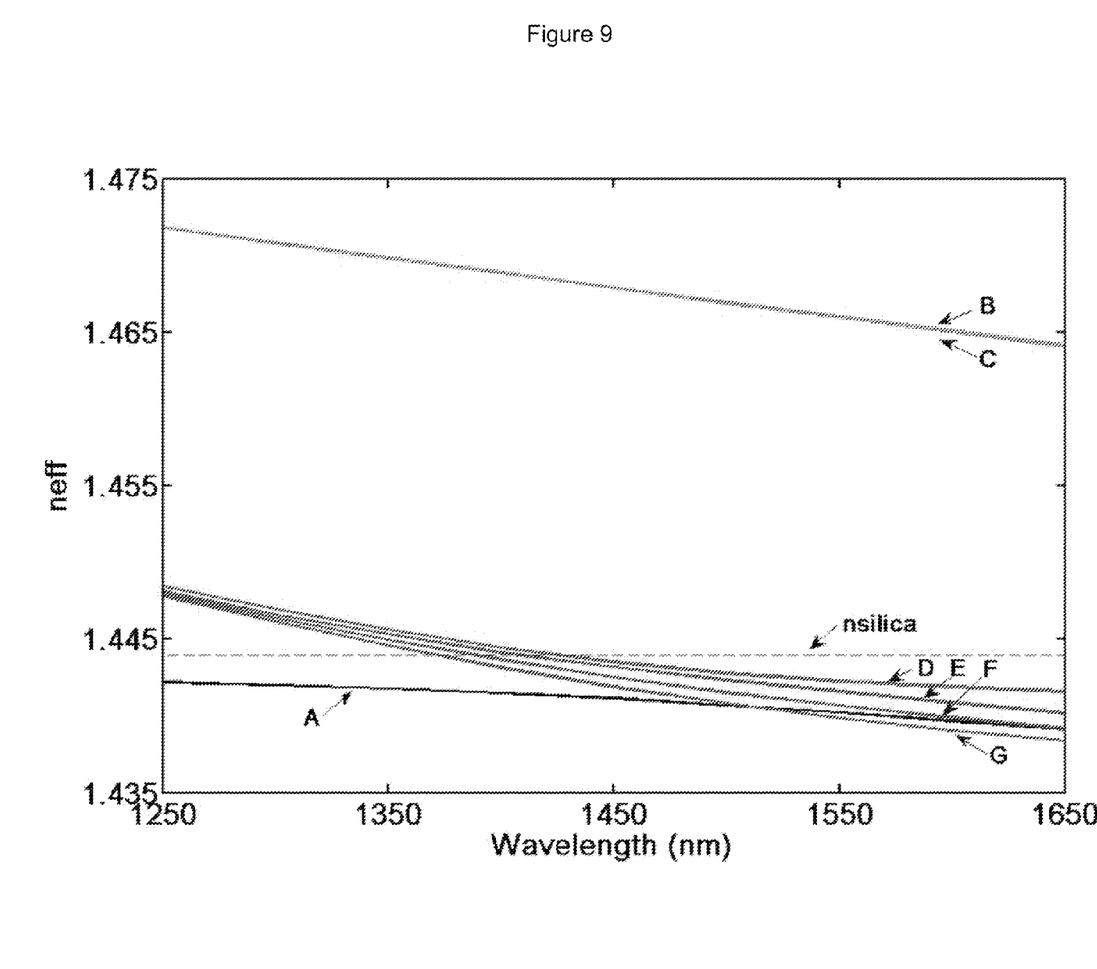
FIG. 9 is a chart depicting a dispersion curve for the mode plotted in FIG. 8 where the broken line is the RI of background silica.

The individual dispersion curve of each mode is also calculated in the wavelength range of 1250~1650 nm, which is the range of the wide band light source used in the experiments, as shown in FIG. 9. The dispersion curves for the fundamental mode and high order rod modes show that light energy coupling cannot easily occur between the core mode and the rod modes even though the rod modes reach their cut-off. Therefore, only the modal interference occurs and a fiber in-line Mach-Zehnder interferometer 9 is created. The temperature sensitivity of the device is measured to be −10.9 nm/° C.

Referring to FIG. 9, only mode G can meet the phase matching condition in the wavelength range. Also, the cut-off wavelength of the $LP_{11}$ like rod modes is not close to the phase matching wavelength compared with that of one hole infiltration.

Figure 12:
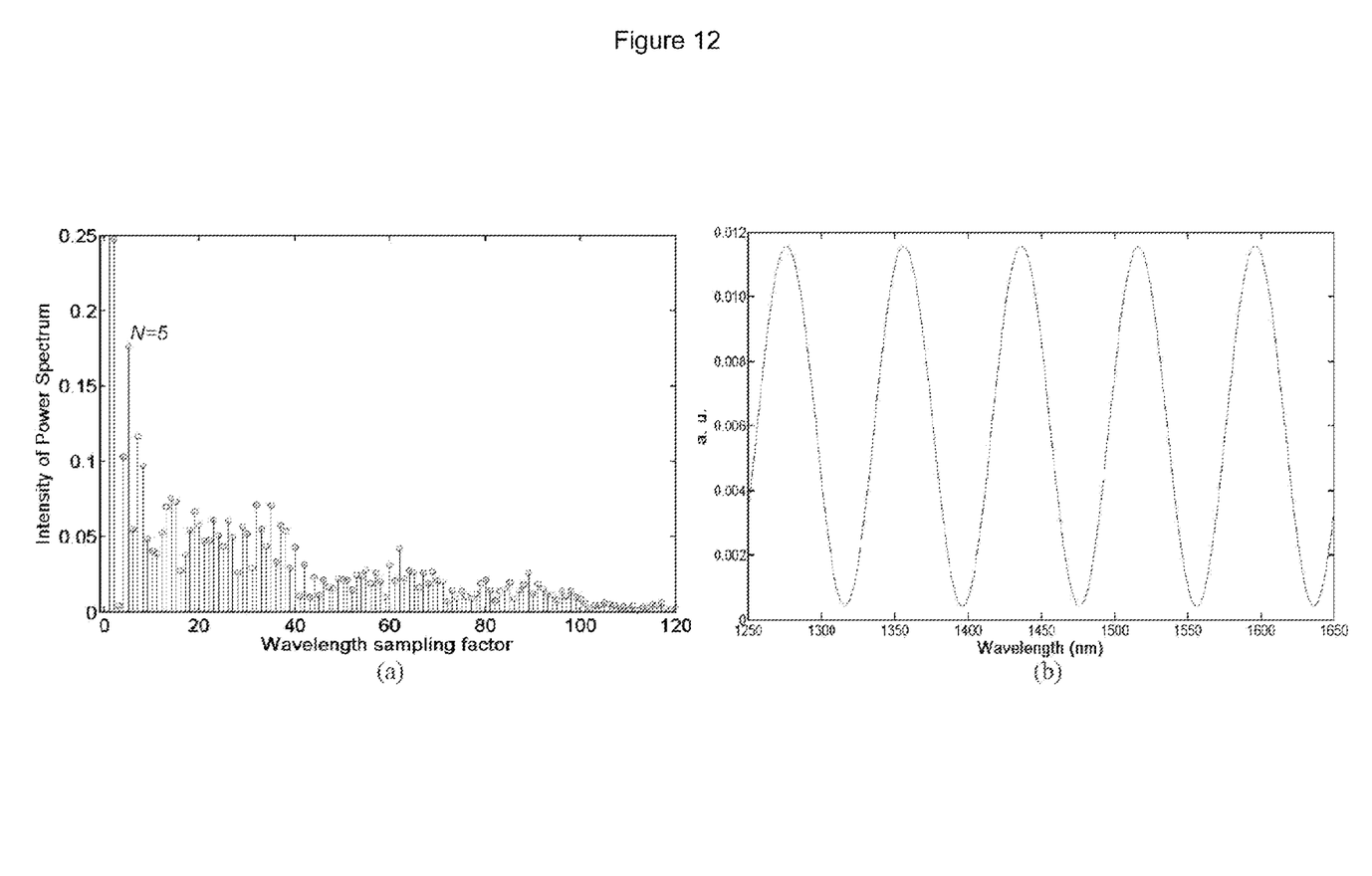
FIG. 12 is set of charts depicting (a) power spectrum of the initial transmission spectrum at 20° C.; and (b) restored interference fringes with normalized amplitude.

According to the theoretical analysis, the interference may occur between the core mode and either of the LP01 rod mode or the $LP_{11}$ rod mode, which means that the transmission spectrum is a multiplexed profile and hence different interference fringe patterns need to be distinguished. In order to decide the free spectral range (FSR) of each fringe pattern, the following mathematical operations are applied: 1) fast Fourier transform (FFT) is performed on the initial transmission spectrum so as to get the power spectrum; 2) filtering, to determine FSR based on the power spectrum and 3) inverse fast Fourier transform (IFFT) is carried out to obtain the individual interference fringe pattern. FIG. 12(a) demonstrates the power spectrum corresponding to the initial transmission spectrum shown in FIG. 1. Because of the modal dispersion, the actual interference fringe pattern is not exactly periodic in wavelength. Each fringe may not have the same visibility. Therefore, the individual interference fringe is hard to be distinguished accurately. Here for Proc. of SPIE Vol. 7753 77530M-3 instance, the strongest component corresponds to a wavelength sampling factor N=5, which means an FSR of 80 nm, as labeled in FIG. 12(a). The interference fringe can be restored after filtering and IFFT, as shown in FIG. 12(b).

According to the theory of two mode interference, $$FSR = \lambda_1 - \lambda_2 = \frac{\lambda_1 \lambda_2}{\Delta n_{off} L}$$

where $\lambda_1$ and $\lambda_2$ are the two wavelengths of the adjacent interference peaks (or dips); $\Delta n_{off} L$ is the difference of the effective RI of the two modes involved and L is the length of the two interference arms. Assuming L=10 cm, the effective RI difference is calculated as $3 \times 10^{-4}$, which corresponds to the interference between the core mode and mode F.

Figure 2:
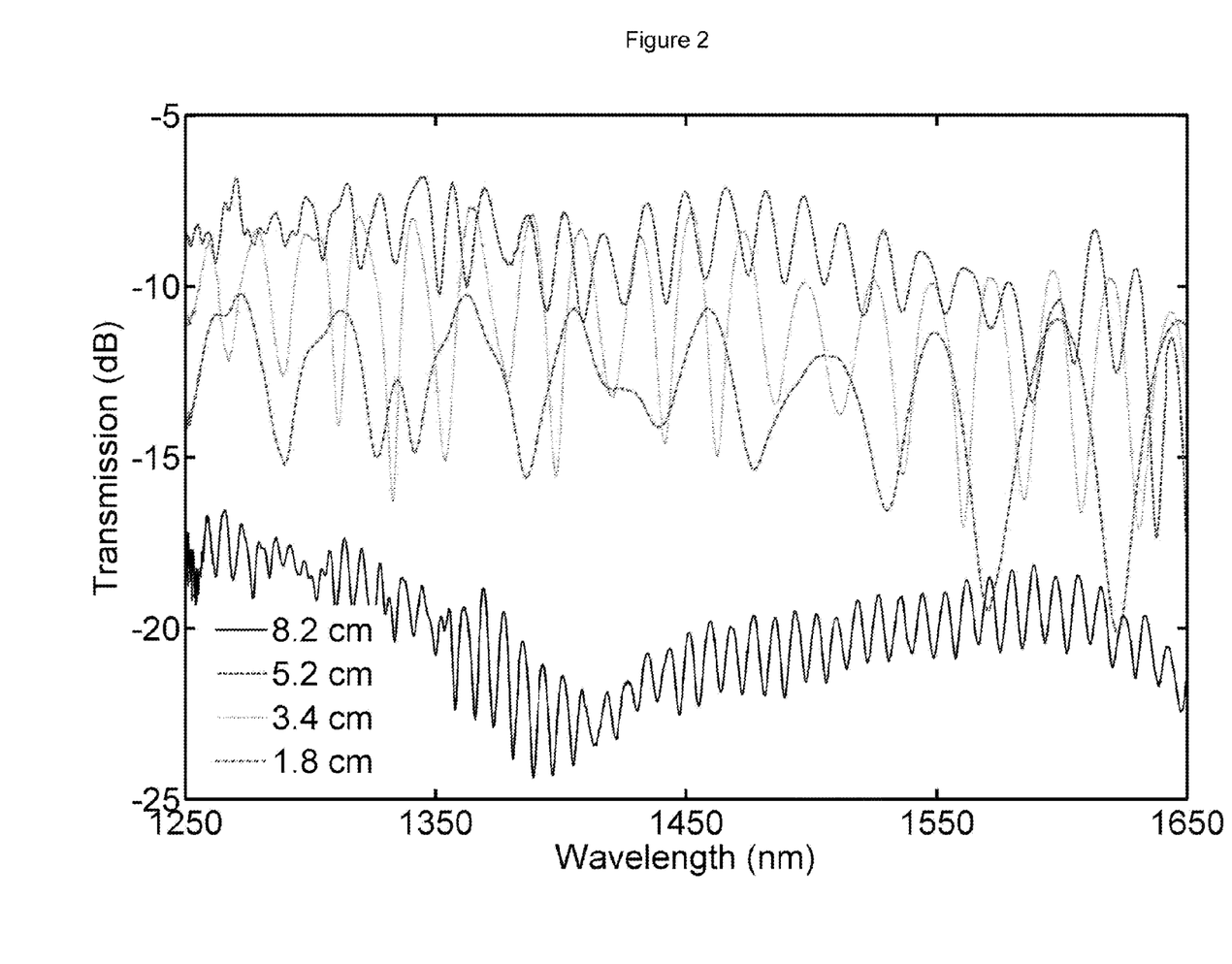
FIG. 2 is a chart depicting transmission spectra for different PCF lengths.

Referring to FIG. 2, after each measurement, the sample is cut back again to allow measuring the transmission spectrum of the device 9 with a different length. It can be clearly seen that an interference fringe pattern exists in every transmission spectrum and the free spectral range (FSR) of the fringe pattern increases with the decrease of PCF length. For example, the FSR around 1550 nm is 8.7, 16.7, 24.2 and 40.2 nm for the PCF length of 8.2, 5.2, 3.4 and 1.8 cm, respectively. The relatively large insertion loss corresponding to the PCF length of 8.2 cm may be created in the splicing process.

According to the theory of two mode interference, $$FSR = \frac{\lambda^2}{\Delta n_{eff} L} \quad \text{Equation (1)}$$

where $\lambda$ is the wavelength of fringe dip (or peak), L is the device length, and $\Delta n_{eff}$ is the difference between the effective RI of the two modes, calculated as $3.4 \times 10^{-3}$, $2.8 \times 10^{-3}$, $3.0 \times 10^{-3}$ and $3.4 \times 10^{-3}$, respectively, for the PCF samples of different lengths. Such a $\Delta n_{eff}$ difference may result from the measurement error of the PCF length. In FIG. 2, the main fringe structure and a slowly varying envelope are found. This is likely due to the interference between the polarization modes, which has a much smaller $\Delta n_{eff}$ and hence a larger FSR than that of the main fringe pattern. However, when the PCF length is reduced, the visibility of the main fringe pattern increases and the slowly varying envelope has little significant effect.

Figure 3:
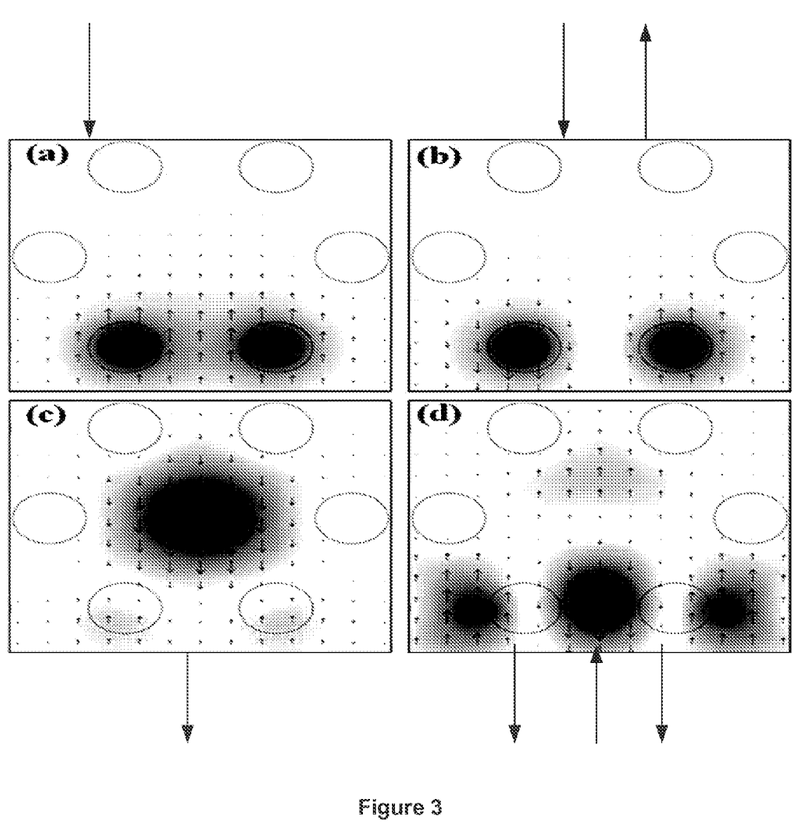
FIG. 3 is a chart depicting simulation of the first four mode fields of PCF with two adjacent holes infiltrate, only y-polarization state is plotted.

Referring to FIG. 3, in order to identify the modes involved in the main interference fringe pattern, the first four modes (each is two folder degenerated) with the largest effective RI values are simulated by the finite element method (FEM). For the sake of simplicity, only one polarization state is plotted. The arrows in FIG. 3 refer to the electrical fields. The modes in FIGS. 3(a) and 3(b) are the bound modes of the high RI rods. Mode (c) is denoted as the PCF fundamental mode and mode (d) is denoted as a virtual core mode confined by the two high RI analyte rods. The virtual core mode is different from the real core mode, and the virtual core mode is supported by the second fiber core. The virtual core mode is actually the overlap of the $LP_{11}$ higher order modes (which is the first higher order mode of the infiltrated holes) of the two high RI rods when they have the same electric field direction. This overlap makes the mode field intensity in the region between the two high RI rods be stronger. The dispersion curves of each mode is shown and is also simulated by use of FEM as shown in FIG. 3.

Figure 4:
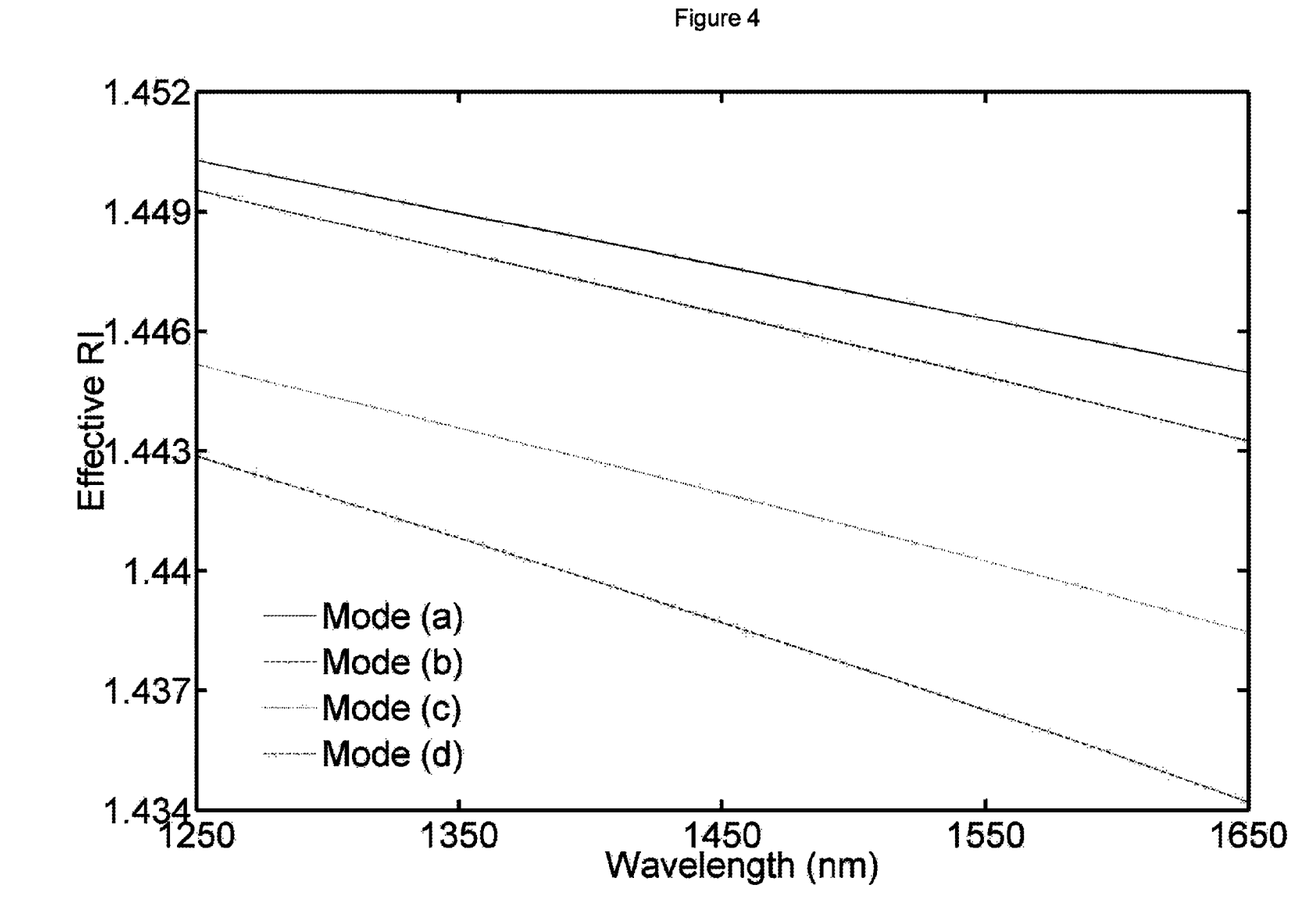
FIG. 4 is a chart depicting dispersion curves of fiber modes shown in FIG. 3.

Referring to FIG. 4, material dispersion is taken into account for the four modes. According to the simulated effective RI value of each mode and the previously calculated $\Delta n_{eff}$, the two modes involved in the main interference pattern should be the PCF fundamental mode and the virtual core mode. The virtual core mode always has a smaller effective RI than that of the background silica, and thus is confined by the hole-silica structure. This is due to the fact that in the wavelength range between 1250 and 1650 nm, the dispersion curves of the PCF fundamental mode and the virtual core mode do not intersect, which means that no mode coupling will occur. This is because the phase matching condition cannot be satisfied as it is different from selective infiltration of air holes in outer layer.

The birefringence of each mode is simulated as $1.1\times10^{-5}$, $5.0\times10^{-6}$, $7.0\times10^{-6}$ and $7.7\times10^{-5}$ for the mode (a)~(d), respectively. The virtual core mode has the largest birefringence, which corresponds to a polarization mode interference with FSR of around 380 nm when the device length is 8.2 cm, similar to that obtained by measuring the slowly varying envelope as shown in FIG. 2.

Figure 5:
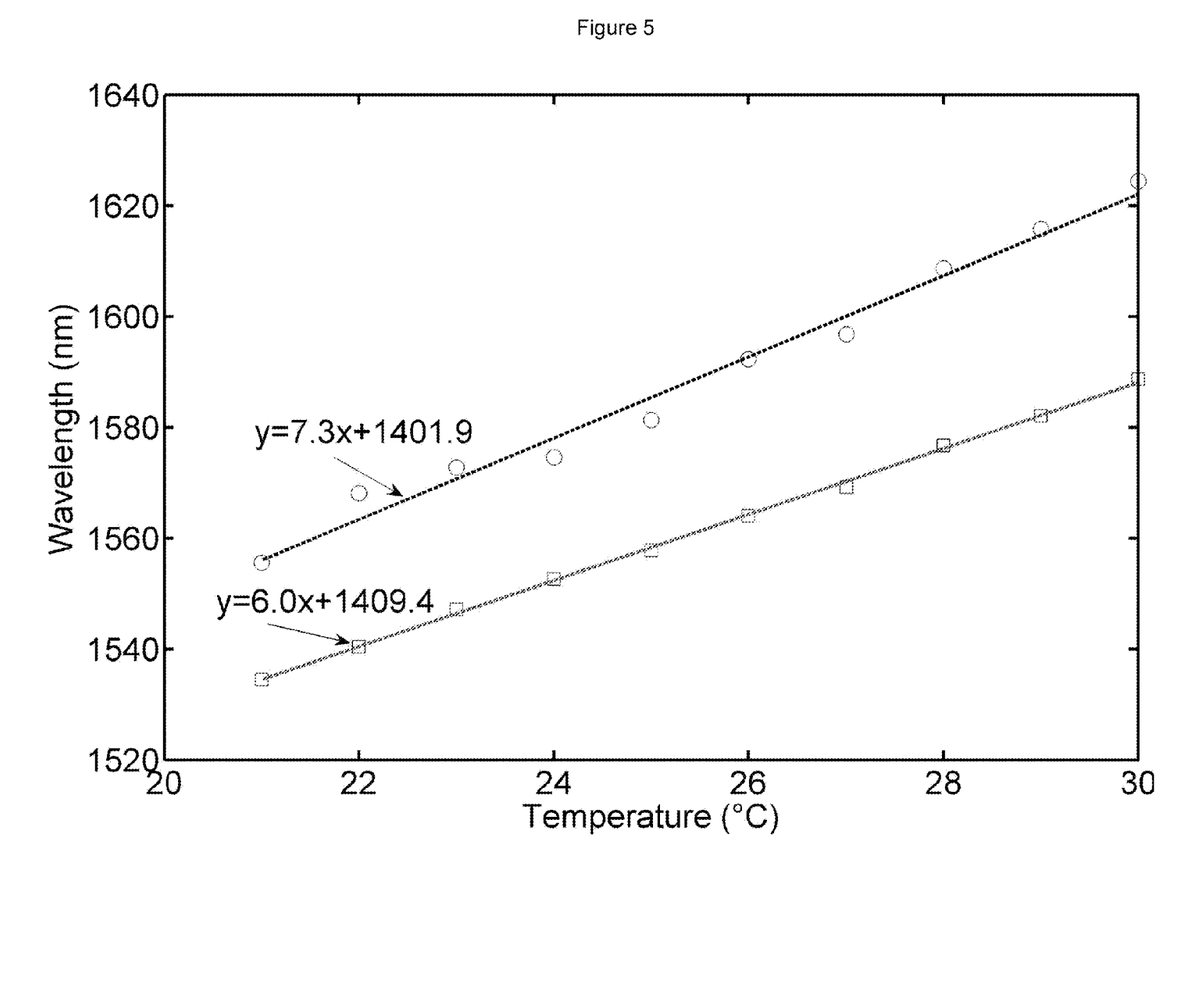
FIG. 5 is a chart depicting fringe wavelength shift with different PCF lengths: circles, 3.4 cm; squares, 1.8 cm; lines: linear fitted.

Referring to FIG. 5, the wavelength shift of the fringe dip corresponding to different PCF lengths are shown. The temperature sensitivity obtained for the PCF length of 1.8 cm and 3.4 cm, is 6.0 nm/° C. and 7.3 nm/° C., respectively. The sensitivity variation may come from the temperature fluctuation during the measurement because of the high temperature sensitivity. A slight temperature fluctuation results in a large measurement error due to the high temperature sensitivity. Although any wavelength dip (peak) can be traced in the measurement, the fringe dip around 1550 nm is chosen (the initial fringe dip is 1555.6 nm and 1534.5 nm for the PCF length of 3.4 cm and 1.8 cm, respectively), which simplifies the subsequent simulations.

For a Mach-Zehnder interferometer, the temperature sensitivity of a certain fringe dip (or peak) is:

$$\frac{d\lambda}{dT} = \frac{\lambda}{n_{eff1} - n_{eff2}} \left( \frac{dn_{eff1}}{dT} - \frac{dn_{eff2}}{dT} \right) \qquad \text{Equation (2)}$$

where $n_{eff1}$ and $n_{eff2}$ are the effective RI of the two modes involved in interference. Since the high RI analyte usually has a much larger thermo coefficient than silica, the temperature sensitivity of the device is much larger than a system based on only a changing RI of silica. For example, the thermo coefficient is $1.2\times10^{-5}$ RIU (refractive index unit)/° C. for silica and $-3.92\times10^{-4}$ RIU/° C. for the high RI liquid infiltrated in the air holes.

Figure 6:
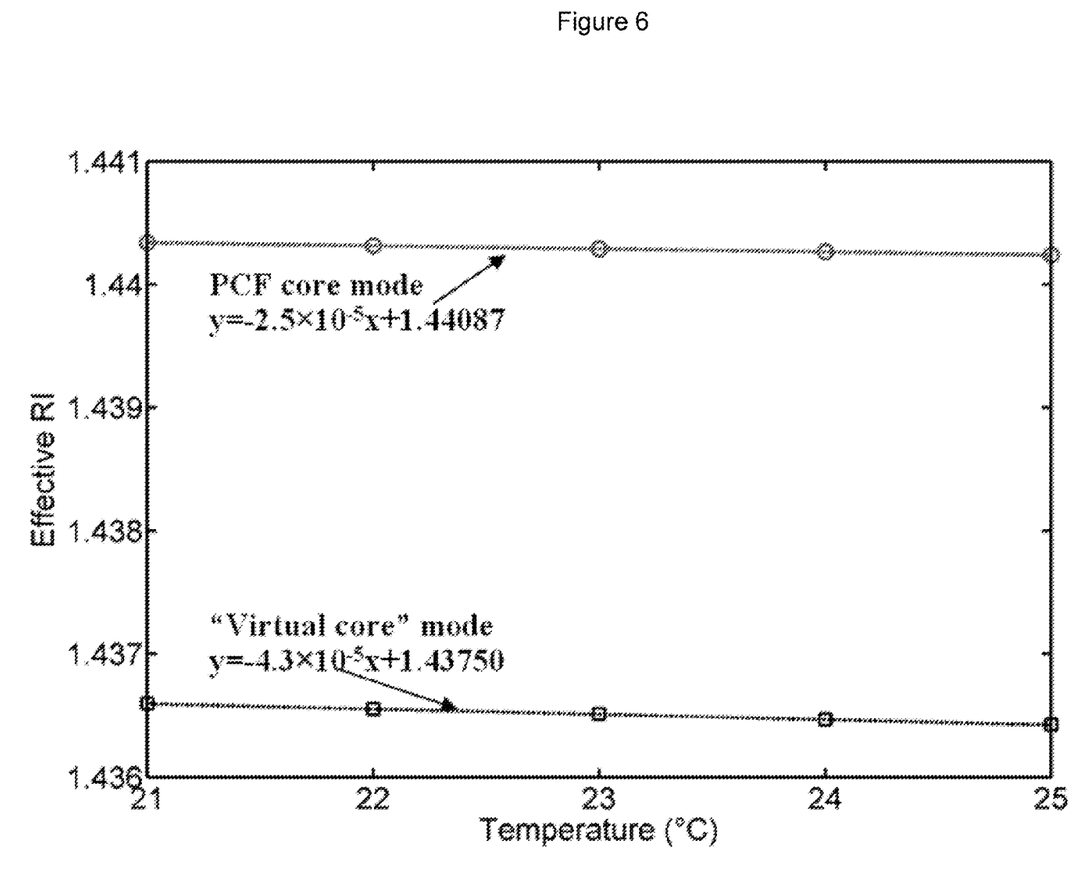
FIG. 6 is a chart of simulated thermo coefficients of the PCF fundamental mode (circles) and the virtual core mode (squares); dotted lines: linear fit of the simulation results.

Referring to FIG. 6, the thermo coefficient of the PCF fundamental mode and the virtual core mode can be simulated accordingly (through FEM) and the results obtained are $-2.5\times10^{-5}$/° C. and $-4.3\times10^{-5}$/° C., respectively.

According to Equation (2), the temperature sensitivity is approximately 8.2 nm/° C., reasonably close to the experiment results obtained in FIG. 5. The temperature sensitivity obtained from the experiment is much larger than that of the air cavity based Mach-Zehnder interferometer or dual core structured PCF. The close values obtained in the experiment and in the simulations also imply that the main interference pattern is most likely produced by the PCF fundamental mode and the virtual core mode.

By selective infiltration of the two adjacent air holes 11 of the innermost layer of PCF 10 with high RI liquid analyte, a virtual core mode can be supported by the electric field coupling between the higher order modes of the high RI rods. This virtual core mode can interfere with the PCF fundamental mode and thus produce an interference fringe pattern in the transmission spectrum. Therefore a fiber in-line Mach-Zehnder interferometer device 9 has been fabricated. Such a fiber in-line Mach-Zehnder interferometer device 9 is robust, exhibits extremely high temperature sensitivity and supports a flexible sensor system operation. Modal analysis shows that the waveguide rod mode has no energy coupling with the fiber core mode and thus only the mode interference can occur. The device 9 has a temperature sensitivity of $-10.9$ nm/° C., which corresponds to a RI sensitivity of $2.7\times104$ nm/RIU. The individual FSR can be decided through a flow of operations including FFT, filtering and IFFT.

It is envisaged that the performance of the device 9 can be enhanced and its field of application can be broadened. For practical example, a material may be selected with a predetermined RI value that can be solidified to form a solid rod in the air hole. The liquid analyte infiltrated in the air holes 11 is able to solidify in the air holes 11 when ultraviolet (UV) light is illuminated. In another embodiment, it is possible that the liquid analyte remains in liquid form in the air holes 11 rather than require solidification so long as an interference fringe pattern is left in the transmission spectrum when light is injected into the PCF.

A data operation procedure may be applied including fast Fourier transform (FFT), filtering and inverse FFT, to enhance the transmission spectra performance of the device 9.

Although two air holes have been described as infiltrated by the liquid analyte, it is possible that more than two air holes may be infiltrated by the liquid analyte. Having more than two air holes infiltrated may still leave an interference fringe pattern in the transmission spectrum when light is injected into the PCF.

Although the air holes that are infiltrated with the liquid analyte have been described as located directly adjacent to a core of the PCF, it is possible that that the air holes that are infiltrated with the liquid analyte may be any of the air holes of the PCF. Having air holes that are not directly adjacent to the core of the PCF infiltrated with the liquid analyte may still leave an interference fringe pattern in the transmission spectrum when light is injected into the PCF.

Although the liquid analyte has been described as having a higher refractive index value than background silica of the PCF such that high RI rods are formed, it is possible that that the liquid analyte may have a slightly lower refractive index value than the background silica of the PCF, or the same refractive index value as the background silica of the PCF. Having lower or the same refractive index value for the liquid analyte may still leave an interference fringe pattern in the transmission spectrum when light is injected into the PCF.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A fiber-inline MZI device for temperature sensing or refractive index (RI) sensing, the device comprising:
    a section of a single core Photonic Crystal Fiber (PCF) formed of a silica material, the PCF having at least two air holes infiltrated with a liquid analyte to form at least two waveguide channels, the liquid analyte forming rods within the PCF;
    wherein the rods form an independent waveguide in the PCF and support rod modes wherein the rod modes are distinct from the core mode transmitted in the PCF;
    wherein the interference between the rod modes and the core mode leaves an interference fringe pattern in the transmission spectrum generated by the PCF when light is injected into the PCF; and
    wherein fringe dips in the fringe pattern when tracked over a wide wavelength range are indicative of at least one of the group consisting of the temperature and refractive index.

2. The device according to claim 1, wherein only two air holes are infiltrated with the liquid analyte.

3. The device according to claim 1, wherein at least one of the air holes that is infiltrated with the liquid analyte is located directly adjacent to a core of the PCF.

4. The device according to claim 1, wherein the liquid analyte has a higher refractive index value than the silica of the PCF such that the rods formed in the PCF are high RI rods.

5. The device according to claim 1, wherein the liquid analyte infiltrated in the air holes is solidified in the air holes by exposing UV light onto the PCF.

6. The device according to claim 1, wherein if the wavelength in the fringe dips shifts towards a shorter wavelength, the temperature is sensed as increasing.

7. The device according to claim 1, wherein the PCF is a NKT Photonics LMA-10, with a hole diameter of 3.04 μm, a hole pitch of 6.26 μm and a length of about 10 cm.

8. The device according to claim 1, wherein the silica has a refractive index of 1.444 and the liquid analyte has a refractive index of 1.47 with a thermo coefficient of $-0.000392/°C$.

9. The device according to claim 1, wherein the liquid analyte substantially fully infiltrates the two air holes of the section of the PCF.

10. A method for manufacturing a fiber-inline MZI device for temperature sensing or refractive index (RI) sensing, comprising:

infiltrating at least two air holes formed in a Photonic Crystal Fiber (PCF) with a liquid analyte to form at least two waveguide channels, the liquid analyte forming rods in the PCF;

incrementally cutting back the PCF until a remaining section of the PCF has the at least two air holes completely filled with the liquid analyte to obtain an infiltrated PCF sample;

wherein the rods leave an interference fringe pattern in the transmission spectrum of the PCF when light is injected into the PCF; and tracking fringe dips in the fringe pattern over a wide wavelength range in order to sense the temperature or refractive index.

11. The method according to claim 10, further comprising fusing the infiltrated PCF sample with a single mode fiber on both ends of the infiltrated PCF sample.

12. The method according to claim 10, further comprising heating the infiltrated PCF sample and recording transmission spectra.

13. The method according to claim 10, further comprising solidifying the liquid analyte after the liquid analyte is infiltrated in the air holes by exposing UV light.

* * * * *